United States Patent
Sun et al.

(10) Patent No.: US 10,258,572 B2
(45) Date of Patent: Apr. 16, 2019

(54) PHARMACEUTICAL COMPOSITIONS OF GOSERELIN SUSTAINED RELEASE MICROSPHERES

(71) Applicant: Shandong Luye Pharmaceutical Co., Ltd., Yantai (CN)

(72) Inventors: Wei Sun, Yantai (CN); Xuemei Zhang, Yantai (CN); Tao Wang, Yantai (CN); Guangyi Leng, Yantai (CN); Kaoxiang Sun, Yantai (CN); Youxin Li, Yantai (CN); Wanhui Liu, Yantai (CN)

(73) Assignee: Shandong Luye Pharmaceutical Co., Ltd., Yantai (CN)

( * ) Notice: Subject to any disclaimer, the term of this patent is extended or adjusted under 35 U.S.C. 154(b) by 0 days.

(21) Appl. No.: 15/789,091

(22) Filed: Oct. 20, 2017

(65) Prior Publication Data

US 2018/0036246 A1    Feb. 8, 2018

Related U.S. Application Data

(63) Continuation of application No. 14/877,976, filed on Oct. 8, 2015, now abandoned, which is a continuation of application No. PCT/CN2014/075441, filed on Apr. 16, 2014.

(30) Foreign Application Priority Data

Apr. 18, 2013    (CN) .......................... 2013 1 0136505

(51) Int. Cl.
| | | |
|---|---|---|
| A61K 9/16 | (2006.01) | |
| A61K 38/09 | (2006.01) | |
| A61P 5/00 | (2006.01) | |
| A61P 13/00 | (2006.01) | |
| A61P 15/00 | (2006.01) | |

(52) U.S. Cl.
CPC .......... *A61K 9/1647* (2013.01); *A61K 9/1641* (2013.01); *A61K 9/1682* (2013.01); *A61K 9/1694* (2013.01); *A61K 38/09* (2013.01)

(58) Field of Classification Search
None
See application file for complete search history.

(56) References Cited

U.S. PATENT DOCUMENTS

| | | |
|---|---|---|
| 2011/0200679 A1 | 8/2011 | Lim et al. |
| 2011/0223247 A1 | 9/2011 | Park et al. |

FOREIGN PATENT DOCUMENTS

| | | |
|---|---|---|
| CN | 101461786 | 6/2009 |
| CN | 101721370 | 6/2010 |
| CN | 102137657 A | 7/2011 |
| JP | 2003-522097 A | 7/2003 |

(Continued)

OTHER PUBLICATIONS

Goserelin, European Parmacopoeia 6.0, 2005-07 (2008), pp. 2005-2007.

(Continued)

*Primary Examiner* — Ernst V Arnold
*Assistant Examiner* — Kyung S Chang
(74) *Attorney, Agent, or Firm* — Seed IP Law Group LLP

(57) ABSTRACT

A composition of goserelin sustained release microspheres is provided. The microspheres comprise goserelin, at least one poly (lactide-co-glycolide) and poloxamer or PEG. The sustained release microspheres have comparatively high bioavailability, which promotes the drug taking its full effect and have entrapment efficiency over 90%.

19 Claims, 4 Drawing Sheets

(56) References Cited

FOREIGN PATENT DOCUMENTS

| JP | 2008-143957 A | 6/2008 |
|---|---|---|
| JP | 2008-150596 A | 7/2008 |
| JP | 2010-513449 A | 4/2010 |
| JP | 2012-508228 A | 4/2012 |
| JP | 2012-193212 A | 10/2012 |
| WO | WO 99/40943 | 8/1999 |
| WO | WO 2008/062908 A1 | 5/2008 |
| WO | WO 2008/066279 A1 | 6/2008 |
| WO | WO 2008/075102 A1 | 6/2008 |
| WO | WO 2012/175538 A1 | 12/2012 |

OTHER PUBLICATIONS

Goserelin, British Pharmacopoeia 2009, British Phamacopoeia vol. I & II, Monographs: Medicinal and Pharmaceutical Substances, © Crown Copyright, 7 pages, (2006).

International Search Report for International Application No. PCT/CN2014/075441 dated Jul. 16, 2014.

Morita, T. et al., "Protein encapsulation into biodegradable microspheres by a novel S/O/W emulsion method using poly(ethylene glycol) as a protein micronization adjuvant," Dec. 2000, pp. 435-444, vol. 69, Journal of Controlled Release.

Zhao, Y., Journal of Modern Clinical Medical, Jul. 2008, vol. 6(7), (English translation of the abstract and discussion section—partial translation).

PHARMACEUTICAL COMPOSITIONS OF GOSERELIN SUSTAINED RELEASE MICROSPHERES

CROSS-REFERENCE TO RELATED APPLICATIONS

This application is a continuation application of U.S. application Ser. No. 14/877,976, filed Oct. 8, 2015, which is a continuation application of International Application No. PCT/CN2014/075441, filed Apr. 16, 2014, which claims priority to Chinese Application No. 201310136505.6, filed Apr. 18, 2013, the contents of each of which are incorporated by reference in their entireties for all purposes.

FIELD OF THE INVENTION

The present disclosure relates to pharmaceutical preparations and, more particularly, to compositions of long-acting sustained release goserelin microspheres, methods for preparing the same and use of the same.

BACKGROUND OF THE INVENTION

Gonadotropin-releasing hormone (GnRH), also known as luteinizing hormone-releasing hormone (LHRH), is a hormone closely related to reproductive functions. When an exogenous LHRH or an analogue thereof is administrated with a physiological pulse frequency (once per 90 min) for a short period of time and at a small dose, it produces some promoting effects to the pituitary-gonadal system, and hence is used clinically for treating symptoms such as sexual dysfunction, anovulation, delayed puberty, etc. When it is administrated with a non-physiological pulse frequency for a long period of time and at a large dose, it can inhibit the hypophysis from secreting luteinizing hormone (LH) and follicle stimulating hormone (FSH), resulting in a decrease in the hormone secretion capacity of gonad and the atrophy of sexual organs. It is thus used clinically for treating some hormone-dependent diseases such as prostate cancer, hysteromyoma, breast carcinoma, adenomyosis, precocious puberty, etc.

Analogues of LHRH regulate the secretion of LH and FSH through feedback inhibition by competitively binding to most of the hypophyseal LHRH receptors, whereby inhibit the produce of ovarian estrogen, and achieve therapeutic effect of medical oophorectomy. Studies have shown that lives of prostate cancer patients can be prolonged by administering hormone analogues of LHRH (such as goserelin) after radiotherapy. Available information has shown that hormone analogues of LHRH are at least able to achieve the same therapeutic effect as surgical castration or CMF chemotherapy, and are used as postoperative adjuvant treatment for premenopausal patients with breast cancer; and achieve the same therapeutic effect as CMF chemotherapy in estrogen receptor-positive patients with axillary lymph node metastasis, with fewer side effects, and more acceptable to the patients. In recent years, goserelin has been used for control of clinical signs and symptoms of endometriosis and adenomyosis to prevent recurrence of endometriosis after surgery, all obtained good results. In addition, goserelin has also been used for endometrium thinning and treatment of uterine fibroids and other symptoms. Several clinical products of LHRH analogues have been commercially available. For example, the goserelin preparation, with the trade name of "Zoladex", has been approved in France in 1987 and approved by FDA On Dec. 29, 1989. Its dosage form is an implant, with a monthly injection dose of 3.6 mg/vial. Adults are subcutaneously injected 3.6 mg once every 28-days at anterior abdominal. However, "for the subcutaneous injection of Zoladex at anterior abdominal, the stype is preloaded in a disposable syringe, and the syringe needle is equivalent in size to the size 16 puncture needle which is 30 mm long, therefore as compared with subcutaneous injection of common drugs, the degree of pain caused by injection of Zoladex is higher and bleeding caused by injection of Zoladex occurs more often."—Journal of Modern Clinical Medical, July, 2008, Volume 6 (7).

According to the characteristics of administration of goserelin to its clinical indications, patients often require long-term administration. Thus, in order to improve patient compliance, goserelin has been developed into long-acting sustained release preparations. Compared with the implant preparations, injecting microsphere preparations to patients significantly reduces the patients' pain and bleeding. Several commercially available LHRH analogues microspheres, such as leuprolide microspheres, adopt this drug release pattern. However, studies have shown that when microspheres are prepared from goserelin to which no pre-treatment is subjected, the drug entrapment efficiency is low and the loss in the manufacturing process is high, resulting in increasing in production cost. Pharmacokinetic studies of the prepared microspheres in animals have shown that the bioavailability of goserelin is low, which makes the drug incapable of acting to its full effect.

SUMMARY OF THE INVENTION

Through in-depth research, we found that by pretreating goserelin with added poloxamer or polyethylene glycol (PEG) therein and then preparing microspheres from the pretreated goserelin increases the drug entrapment efficiency and improves the bioavailability of the drug, which promotes the drug taking its full effect.

The present disclosure provides a pharmaceutical composition of sustained release goserelin microspheres. The goserelin microspheres comprise (a) goserelin or a salt thereof, (b) copolymers of lactide and glycolide (poly(lactide-co-glycolide; PLGA), and (c) poloxamer or polyethylene glycol (PEG).

In the pharmaceutical composition of sustained release goserelin microspheres of the present disclosure, the content by weight of goserelin or the salt thereof may be 1-10%, preferably 1-8%, more preferably 1-5%. The content by weight of the copolymers of lactide and glycolide may be 80-98%, preferably 86-98%, more preferably 91-98%. The content by weight of the poloxamer or polyethylene glycol may be 1-10%, preferably 1-6%, more preferably 1-4%.

The pharmaceutical composition may further comprise less than 0.1% by weight of (d) acetic acid, preferably less than 0.01%, more preferably 0.008%.

In one pharmaceutical composition, the weight content of the goserelin is 1-10%; the weight content of the poly(lactide-co-glycolide) is 80-98%; and the weight content of the poloxamer or PEG is 1-10%.

In another pharmaceutical composition, the weight content of the goserelin is 1-8%; the weight content of the poly(lactide-co-glycolide) is 86-98%; and the weight content of the poloxamer or PEG is 1-6%.

In yet another pharmaceutical composition, the weight content of the goserelin is 1-5%; the weight content of the poly(lactide-co-glycolide) is 91-98%; and the weight content of poloxamer or PEG is 1-4%.

The copolymer of lactide and glycolide is also referred to as poly(lactide-co-glycolide), abbreviated as PLGA. The molar ratio of lactide to glycolide in said PLGA may be 90:10 to 10:90, preferably 75:25 to 25:75, more preferably 60:40 to 40:60, most preferably 50:50.

The intrinsic viscosity of poly (lactide-co-glycolide) (PLGA) may be 0.10-0.40 dL/g, preferably in the range of 0.10-0.35 dL/g, more preferably in the range of 0.10-0.30 dL/g. A method for measuring the intrinsic viscosity of PLGA may be as follows: prepare an about 0.5% (w/v) solution of PLGA in chloroform, and determine the intrinsic viscosity of PLGA at 30° C. using a Cannon-Fenske glass capillary viscometer.

The PLGA described in the present disclosure may have a molecular weight of 4,000-45,000 Dalton, preferably 4,000-35,000 Dalton, more preferably 4,000-30,000 Dalton. As used herein, the term "molecular weight" refers to "weight average molecular weight."

For convenience of description, the molar ratio of lactide to glycolide, the intrinsic viscosity and molecular weight of PLGA are shown hereinafter in brackets following each PLGA. For example, "PLGA (50/50, 0.14, 7,200)" represents poly (lactide-co-glycolide) with a molar ratio of lactide to glycolide of 50:50, an intrinsic viscosity of 0.14 dL/g, and a molecular weight of 7,200 Dalton.

The poloxamers described in the present disclosure are block copolymers of polyethylene glycol and polypropylene glycol. The copolymers are composed of various compounds with different hydrophile-lipophile balance and are formed by appropriate amount of polyoxypropylene and appropriate amount of polyoxyethylene. The preferred poloxamers is Poloxamer 188 or Poloxamer 407, more preferably Poloxamer 188.

The polyethylene glycol (PEG) described in the present disclosure, also known as polymer of $\alpha$-hydrogen-$\omega$-hydroxy(oxy-1,2-ethanediyl) or polyoxyethylene (PEO-LS), is a general term for glycol polymer. The polyethylene glycol may be PEG 2000, PEG 4000 or PEG 6000, preferably PEG 6000.

The drug loading amount is the actual drug loading amount, which may be calculated as follows: drug loading amount=[amount of drug in microspheres/(amount of drug in microspheres+amount of polymeric excipients)]×100% (I), wherein the polymeric excipients include polymers disclosed in the present disclosure, for example the combination of PLGA and poloxamers or the combination of PLGA and polyethylene glycol.

The entrapment efficiency may be calculated as follows: entrapment efficiency (%)=[measured drug loading amount in microspheres/(theoretical drug loading amount in microspheres)]×100% (II), wherein the "measured drug loading amount in microspheres" in formula (II) is the "drug loading amount" calculated according to formula (I); wherein the "theoretical drug loading amount in microspheres" is calculated according to formula (I) based on the amount of the drug and the amount of the polymeric excipients measured separately before they are combined for the preparation of microspheres.

The salt of goserelin in the sustained release microspheres provided by the present disclosure may be any water-soluble salt such as an acetate salt.

For each pharmaceutical composition of the sustained release goserelin microspheres of the present disclosure, a preparation method is provided. The method involves a solid-in-oil-in-water (s/o/w) emulsion-solvent evaporation process. The process comprises pre-treating goserelin acetate with poloxamer or PEG, and then adding the pre-treated goserelin acetate to an oil phase comprising poly(lactide-co-glycolide). The poloxamer or PEG pre-treated goserelin acetate in the oil phase may have a particle size d (0.5) of 0.01-2 μm.

Goserelin acetate may be pretreated by mixing the goserelin acetate with poloxamer or polyethylene glycol to form a solid powder mixture; PLGA is dissolved in an organic solvent to form an oil phase; the solid powder mixture is added into the oil phase, and then subjected to shearing emulsification to obtain a solid-in-oil (s/o) primary emulsion. Then, the primary emulsion is added into an aqueous solution containing an emulsifier, homogeneously emulsified to obtain an S/O/W double emulsion, then the organic solvent is removed from the S/O/W double emulsion, and the residue is washed and filtered to obtain the microspheres.

The organic solvent may be ethyl acetate, chloroform or dichloromethane, preferably dichloromethane.

The emulsifiers may be hydrophilic emulsifiers, for example, tweens, polyethylene glycol octylphenol ether (Triton), Brij, Poly polyvinyl pyrrolidone or polyvinyl alcohol, preferably polyvinyl alcohol (PVA).

The concentration of emulsifier in the aqueous solution may be 0.01%-5%, preferably 0.02-2%, more preferably 0.5%-1.0%.

The present disclosure provides a use of the goserelin microspheres in preparation of drugs for treating prostate cancer, sexual precocity, adenomyosis, female infertility, and hysteromyoma.

The present disclosure also provides a method for treating prostate cancer, sexual precocity, adenomyosis, female infertility, or hysteromyoma in a subject in need thereof. The treatment method comprises administering to the subject an effective amount of the pharmaceutical composition of sustained release goserelin microspheres described in the present disclosure. The subject may be an animal, preferably a mammal, more preferably a human. The pharmaceutical composition of the present invention may be formulated for oral, sublingual, intranasal, intraocular, rectal, transdermal, mucosal, topical or parenteral administration. Parenteral administration may include intradermal, subcutaneous (s.c., s.q., sub-Q, Hypo), intramuscular (i.m.), intravenous (i.v.), intraperitoneal (i.p.), intra-arterial, intramedulary, intracardiac, intra-articular (joint), intrasynovial (joint fluid area), intracranial, intraspinal, and intrathecal (spinal fluids) injection or infusion, preferably intraperitoneal (i.p.) injection in mouse and intravenous (i.v.) in human. Any device suitable for parenteral injection or infusion of drug formulations may be used for such administration. For example, the pharmaceutical composition may be contained in a sterile pre-filled syringe.

The microspheres provided by the present invention may be made into the form of sterile powder, wherein the sterile powder may comprise the composition of goserelin microspheres and mannitol, and may be prepared as follows: rinsing the composition of goserelin microspheres with water for injection and transferring into a freeze-drying tray, adding mannitol and a proper amount of water for injection therein, placing the freeze-drying tray in a freeze drier for freeze-drying; and subjecting the freeze-dried product to sieving and mixing, aseptic filling and capping, so as to obtain the sterile powder. Before being administrated to a patient, the sterile powder may be suspended in a pharmaceutically acceptable dispersion solvent, wherein the dispersion solvent may comprise a suspending agent, a pH regulator, an isoosmotic adjusting agent, a surfactant, or a combination thereof, together with water for injection; the suspending agent may be selected from the group consisting of sodium carboxymethyl cellulose, polyvinyl alcohol, polyvinylpyrrolidone, sodium alginate, glycerol, and a combination thereof; the isoosmotic adjusting agent may be selected from the group consisting of sodium chloride, glucose, mannitol, sorbitol and a combination thereof; and the surfactant may be a nonionic surfactant such as polysorbate series (e.g., polysorbate 80, polysorbate 60, etc.). The sustained release goserelin microspheres provided by the present disclosure may be used for intramuscular or subcutaneous injection.

The sustained release goserelin microspheres described in the present disclosure may have high entrapment efficiency over, for example, 80%, 90%, 95% or 99%, preferably 90%, when goserelin is pretreated by poloxamer or PEG, and may have relatively high bioavailability in vivo of, for example, at least 1%, 5%, 10%, 20%, 30%, 40% or 50% in a subject after administration.

A pharmaceutical composition of sustained release goserelin microspheres according to the present invention may have higher entrapment efficiency than a control composition by, for example, by at least 1%, 5%, 10%, 20%, 30%, 40%, 50%, 60%, 70%, 80%, 90%, or 95%. The control composition is identical to the pharmaceutical composition except having no or less poloxamer or polyethylene glycol (PEG).

When administered to a subject in need thereof, a pharmaceutical composition of sustained release goserelin microspheres according to the present invention may have higher bioavailability in the subject than a control composition by, for example, at least 1%, 5%, 10%, 20%, 30%, 40%, 50%, 60%, 70%, 80%, 90%, or 95%. The control composition is identical to the pharmaceutical composition except having no or less poloxamer or polyethylene glycol (PEG). For example, when administered to a subject in need thereof, a pharmaceutical composition of the present invention having at least 1% poloxamer or polyethylene glycol (PEG) may have at least 20% higher bioavailability in the subject than a control composition lacking the poloxamer or polyethylene glycol (PEG).

The particle size span used in the present disclosure is defined according to the Guidelines for Microcapsules, Microspheres and Liposome Preparations, Appendix XIXE of Chinese Pharmacopoeia (2010 Edition) as follows:

$$\text{Span}=(D90-D10)/D50$$

wherein, D90, D50 and D10 refer to the particle sizes respectively corresponding to 90%, 50% and 10% of the cumulative distribution in the cumulative curve. The smaller the span is, the narrower the distribution and thus the more uniform the particle size.

DETAILED DESCRIPTION OF THE INVENTION

Figure 1:
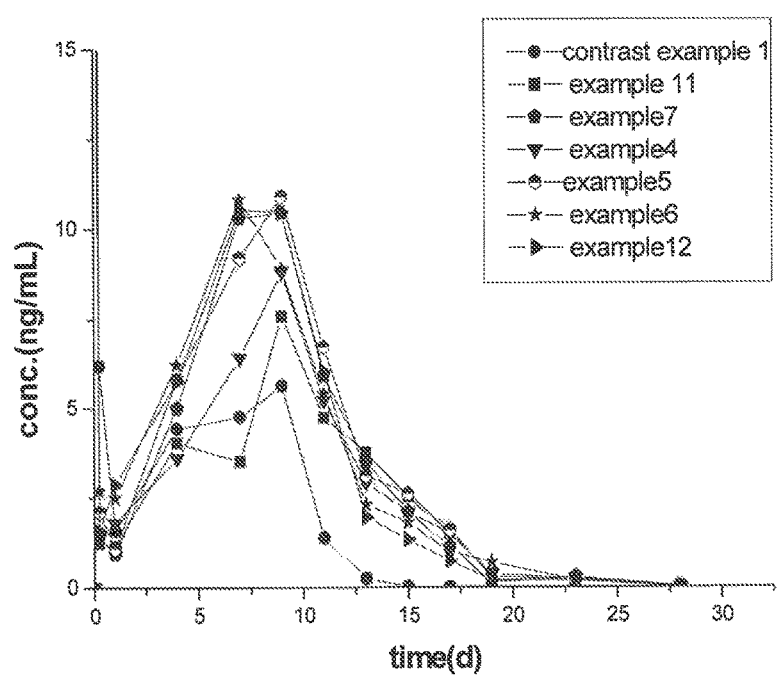
FIG. 1 is a graph of rat in vivo drug release curves of goserelin microspheres which contain different amount of poloxamer/PEG.

The present disclosure will be further illustrated by the following examples and test examples, which will not limit the scope of the present invention in any way.

Example 1

Appropriate amount of goserelin acetate and Poloxamer 188 were weighed and ball-mill mixed at frequency of 15 Hz for 5 min so as to obtain a mixture of solid powder. 430 mg mixture of goserelin and Poloxamer 188 (the measured amount of goserelin was 215 mg) was accurately weighed for later use. 1.721 g of PLGA (75/25, 0.35, 42,000) was weighed and dissolved in 10 ml of dichloromethane to form an oil phase; and then the pretreated drug mixture of solid powder was added into the oil phase, and subjected to emulsification in a high shear emulsifier (6,500 rpm, 3 min) so as to obtain a s/o primary emulsion. The primary emulsion was added into 1,000 ml of a 0.5% PVA solution at 6° C. under homogenization at 1,800 rpm, and then it was homogeneously emulsified for 2 min to obtain an S/O/W double emulsion. The double emulsion was stirred to volatilize and remove the organic solvent; the residue was washed and freeze-dried to obtain powdery microspheres. The microspheres had a drug loading amount of 9.01% and an entrapment efficiency of 90.1%.

Example 2

The melting temperature of a melt extruder was set at 80° C. Appropriate amount of goserelin acetate and Poloxamer 407 were sifted and mixed. The mixture was fed into the cavity of the extruder. The stirring speed was set to n=60 and the stirring mixing time to 3 min. Then the valve handle was released to extrude the melted material, which was then allowed to become cool naturally. The material was ball-mill smashed for 2 min. 316 mg of the mixture of goserelin and Poloxamer 188 (the measured amount of goserelin was 158 mg) was accurately weighed for later use. 1.672 g of PLGA (25/75, 0.24, 25,000) was weighed and dissolved in 10 ml of dichloromethane to form an oil phase; and then the pretreated drug mixture of solid powder was added into the oil phase, and subjected to emulsification in a high shear emulsifier (6,500 rpm, 3 min) so as to obtain a s/o primary emulsion. The primary emulsion was added into 1,000 ml of a 0.5% PVA solution at 6° C. under homogenization at 1,800 rpm, and then it was homogeneously emulsified for 2 min to obtain an S/O/W double emulsion. The double emulsion was stirred to volatilize and remove the organic solvent; the residue was washed and freeze-dried to obtain powdery microspheres. The microspheres had a drug loading amount of 7.21% and an entrapment efficiency of 90.7%.

Example 3

Appropriate amount of goserelin acetate and Poloxamer 188 were weighed and dissolved in water to form a clear solution, and then the solution was sprayed dried so as to obtain a mixture of solid powder. 47 mg spray-dried mixture of goserelin and Poloxamer 188 (the measured amount of goserelin was 23 mg) was accurately weighed and put into a vial. 1.951 g of PLGA (65/35, 0.29, 32,000) was weighed and dissolved in 10 ml of dichloromethane to form an oil phase; and then the pretreated drug mixture of solid powder was added into the oil phase, and subjected to emulsification in a high shear emulsifier (6,500 rpm, 3 min) so as to obtain a s/o primary emulsion. The primary emulsion was added into 1,000 ml of a 0.5% PVA solution at 6° C. under homogenization at 1,800 rpm, and then it was homogeneously emulsified for 2 min to obtain an S/O/W double emulsion. The double emulsion was stirred to volatilize and remove the organic solvent; the residue was washed and freeze-dried to obtain powdery microspheres. The microspheres had a drug loading amount of 1.02% and an entrapment efficiency of 90.1%.

Example 4

92 mg of goserelin acetate (containing 80 mg of goserelin as measured) and 21 mg of Poloxamer 188 were weighed and dissolved in 10 ml of water to form a clear solution, and then the solution was freeze-dried so as to obtain a mixture of solid powder. 1.908 g of PLGA (50/50, 0.14, 7,200) was weighed and dissolved in 10 ml of dichloromethane to form an oil phase; and then the pretreated drug mixture of solid powder was added into the oil phase, and subjected to emulsification in a high shear emulsifier (6,500 rpm, 3 min) so as to obtain a s/o primary emulsion. The primary emulsion was added into 1,000 ml of a 0.5% PVA solution at 6° C. under homogenization at 1,800 rpm, and then it was homogeneously emulsified for 2 min to obtain an S/O/W double emulsion. The double emulsion was stirred to volatilize and remove the organic solvent; the residue was washed and freeze-dried to obtain powdery microspheres: The microspheres had a drug loading amount of 3.62% and an entrapment efficiency of 91.4%.

Example 5

83 mg of goserelin acetate (containing 72 mg of goserelin as measured) and 41 mg of Poloxamer 188 were weighed and dissolved in 10 ml of water to form a clear solution, and then the solution was freeze-dried so as to obtain a mixture of solid powder. 1.876 g PLGA (50/50, 0.14, 7,200) was weighed and dissolved in 10 ml of dichloromethane to form an oil phase; and then the pretreated drug mixture of solid powder was added into the oil phase, and subjected to emulsification in a high shearing emulsifier (6500 rpm, 3 min) so as to obtain a s/o primary emulsion. The primary emulsion was added into 1,000 ml of a 0.5% PVA solution at 6° C. under homogenization at 1,800 rpm, and then it was homogeneously emulsified for 2 min to obtain an S/O/W double emulsion. The double emulsion was stirred to volatilize and remove the organic solvent; the residue was washed and freeze-dried to obtain powdery microspheres. The microspheres had a drug loading amount of 3.56% and an entrapment efficiency of 98.6%.

Example 6

91 mg of goserelin acetate (containing 79 mg of goserelin as measured) and 101 mg of Poloxamer 188 were weighed and dissolved in 20 ml of water to form a clear solution, and then the solution was freeze-dried so as to obtain a mixture of solid powder. 1.811 g PLGA (50/50, 0.14, 7,200) was weighed and dissolved in 10 ml of dichloromethane to form an oil phase; and then the pretreated drug mixture of solid powder was added into the oil phase, and subjected to emulsification in a high shearing emulsifier (6,500 rpm, 3 min) so as to obtain a s/o primary emulsion. The primary emulsion was added into 1,000 ml of a 0.5% PVA solution at 6° C. under homogenization at 1,800 rpm, and then it was homogeneously emulsified for 2 min to obtain an S/O/W double emulsion. The double emulsion was stirred to volatilize and remove the organic solvent; the residue was washed and freeze-dried to obtain powdery microspheres. The microspheres had a drug loading amount of 3.61% and an entrapment efficiency of 91.3%.

Example 7

92 mg of goserelin acetate (containing 80 mg of goserelin as measured) and 201 mg of Poloxamer 188 were weighed and dissolved in 20 ml of water to form a clear solution, and then the solution was freeze-dried so as to obtain a mixture of solid powder. 1.723 g PLGA (50/50, 0.14, 7,200) was weighed and dissolved in 10 ml of dichloromethane to form an oil phase; and then the pretreated drug mixture of solid powder was added into the oil phase, and subjected emulsification in a high shearing emulsifier (6,500 rpm, 3 min) so as to obtain a s/o primary emulsion. The primary emulsion was added into 1000 ml of a 0.5% PVA solution at 6° C. under homogenization at 1800 rpm, and then it was homogeneously emulsified for 2 min to obtain an S/O/W double emulsion. The double emulsion was stirred to volatilize and remove the organic solvent; the residue was washed and freeze-dried to obtain powdery microspheres. The microspheres had a drug loading amount of 3.58% and an entrapment efficiency of 90.2%.

Example 8

62 mg of goserelin acetate (containing 54 mg of goserelin as measured) and 41 mg of Poloxamer 188 were weighed and dissolved in 10 ml of water to form a clear solution, and then the solution was freeze-dried so as to obtain a mixture of solid powder. PLGA (50/50, 0.14, 7,200) and PLGA (0/50, 0.20, 18,000) with weight ratio of 1:1 were weighed and a total of 1.964 g of PLGAs were dissolved in 10 ml of dichloromethane to form an oil phase; and then the pretreated drug mixture of solid powder was added into the oil phase, and subjected to emulsification in a high shearing emulsifier (6,500 rpm, 3 min) so as to obtain a s/o primary emulsion. The primary emulsion was added into 1,000 ml of a 0.5% PVA solution at 6° C. under homogenization at 1,800 rpm, and then it was homogeneously emulsified for 2 min to obtain an S/O/W double emulsion. The double emulsion was stirred to volatilize and remove the organic solvent; the residue was washed and freeze-dried to obtain powdery microspheres. The microspheres had a drug loading amount of 2.54% and an entrapment efficiency of 97.3%.

Example 9

26 mg of goserelin acetate (containing 23 mg of goserelin as measured) and 58 mg of Poloxamer 188 were weighed and dissolved in 10 ml of water to form a clear solution, and then the solution was freeze-dried so as to obtain a mixture of solid powder. PLGA (50/50, 0.14, 7,200) and PLGA (0/50, 0.20, 18,000) with weight ratio of 1:3 were weighed and a total of 1.801 g PLGAs were dissolved in 10 ml of dichloromethane to form an oil phase; and then the pretreated drug mixture of solid powder was added into the oil phase, and subjected to emulsification in a high shearing emulsifier (6,500 rpm, 3 min) so as to obtain a s/o primary emulsion. The primary emulsion was added into 1,000 ml of a 0.5% PVA solution at 6° C. under homogenization at 1,800 rpm, and then it was homogeneously emulsified for 2 min to obtain an S/O/W double emulsion. The double emulsion was stirred to volatilize and remove the organic solvent; the residue was washed and freeze-dried to obtain powdery microspheres. The microspheres had a drug loading amount of 1.15% and an entrapment efficiency of 95.8%.

Example 10

129 mg of goserelin acetate (containing 112 mg of goserelin as measured) and 82 mg of Poloxamer 188 were weighed and dissolved in 10 ml of water to form a clear solution, and then the solution was freeze-dried so as to obtain a mixture of solid powder. PLGA (50/50, 0.14, 7,200) and PLGA (50, 0.20, 18,000) with weight ratio of 3:1 were weighed and a total of 1.861 g PLGAs were dissolved in 10 ml of dichloromethane to form an oil phase; and then the pretreated drug mixture of solid powder was added into the oil phase, and subjected to emulsification in a high shearing emulsifier (6,500 rpm, 3 min) so as to obtain a s/o primary emulsion. The primary emulsion was added into 1,000 ml of a 0.5% PVA solution at 6° C., under homogenization at 1,800 rpm, and then it was homogeneously emulsified for 2 min to obtain an S/O/W double emulsion. The double emulsion was stirred to volatilize and remove the organic solvent; the residue was washed and freeze-dried to obtain powdery microspheres. The microspheres had a drug loading amount of 5.31% and an entrapment efficiency of 98.0%.

Example 11

91 mg of goserelin acetate (containing 79 mg of goserelin as measured) and 6 mg of Poloxamer 188 were weighed and dissolved in 10 ml of water to form a clear solution, and then the solution was freeze-dried so as to obtain a mixture of solid powder. 1.924 g PLGA (50/50, 0.14, 7,200) was weighed and dissolved in 10 ml of dichloromethane to form an oil phase; and then the pretreated drug mixture of solid powder was added into the oil phase, and subjected to emulsification in a high shearing emulsifier (6,500 rpm, 3 min) so as to obtain a s/o primary emulsion. The primary emulsion was added into 1,000 ml of a 0.5% PVA solution at 6° C. under homogenization at 1,800 rpm, and then it was homogeneously emulsified for 2 min to obtain an S/O/W double emulsion. The double emulsion was stirred to volatilize and remove the organic solvent; the residue was washed and freeze-dried to obtain powdery microspheres. The microspheres had a drug loading amount of 2.98% and an entrapment efficiency of 76.1%.

Example 12

93 mg of goserelin acetate (containing 81 mg of goserelin as measured) and 41 mg of PEG6000 were weighed and dissolved in 10 ml of water to form a clear solution, and then the solution was freeze-dried so as to obtain a mixture of solid powder. 1.931 g PLGA (50/50, 0.14, 7,200) was weighed and dissolved in 10 ml of dichloromethane to form an oil phase; and then the pretreated drug mixture of solid powder was added into the oil phase, and subjected to emulsification in a high shearing emulsifier (6,500 rpm, 3 min) so as to obtain a s/o primary emulsion. The primary emulsion was added into 1,000 ml of a 0.5% PVA solution at 6° C. under homogenization at 1,800 rpm, and then it was homogeneously emulsified for 2 min to obtain an S/O/W double emulsion. The double emulsion was stirred to volatilize and remove the organic solvent; the residue was washed and freeze-dried to obtain powdery microspheres. The microspheres had a drug loading amount of 3.64% and an entrapment efficiency of 92.9%.

Example 13

90 mg of goserelin acetate (containing 78 mg of goserelin as measured) and 42 mg of PEG4000 were weighed and dissolved in 10 ml of water to form a clear solution, and then the solution was freeze-dried so as to obtain a mixture of solid powder. 1.925 g PLGA (85/15, 0.36, 44,000) was weighed and dissolved in 10 ml of dichloromethane to form an oil phase. The pretreated drug mixture of solid powder was added into the oil phase, and then subjected to emulsification in a high shearing (6,500 rpm, 3 min) so as to obtain a s/o primary emulsion. The primary emulsion was added into 1,000 ml of a 0.5% PVA solution at 6° C. under homogenization at 1,800 rpm, and then it was homogeneously emulsified for 2 min to obtain an S/O/W double emulsion. The double emulsion was stirred to volatilize and remove the organic solvent; the residue was washed and freeze-dried to obtain powdery microspheres. The microspheres had a drug loading amount of 3.43% and an entrapment efficiency of 90.1%.

Example 14

94 mg of goserelin acetate (containing 82 mg of goserelin as measured) and 42 mg of PEG2000 were weighed and dissolved in 20 ml of water to form a clear solution, and then the solution was freeze-dried so as to obtain a mixture of solid powder. 1.923 g PLGA (10/90, 0.27, 29,000) was weighed and dissolved in 10 ml of dichloromethane to form an oil phase; and then the pretreated drug mixture of solid powder was added into the oil phase, and subjected to emulsification in a high shearing emulsifier (6,500 rpm, 3 min) so as to obtain a s/o primary emulsion. The primary emulsion was added into 1,000 ml of a 0.5% PVA solution at 6° C. under homogenization at 1,800 rpm, and then it was homogeneously emulsified for 2 min to obtain an S/O/W double emulsion. The double emulsion was stirred to volatilize and remove the organic solvent; the residue was washed and freeze-dried to obtain powdery microspheres. The microspheres had a drug loading amount of 3.59% and an entrapment efficiency of 90.4%.

Comparative Example 1

93 mg of goserelin acetate (containing 81 mg of goserelin as measured) was weighed and dissolved in 4 ml of water to form a clear solution, and then the solution was freeze-dried so as to obtain a mixture of solid powder. 1.908 g PLGA (50/50, 0.14, 7,200) was weighed and dissolved in 10 ml of dichloromethane to form an oil phase; and then the pretreated drug mixture of solid powder was added into the oil phase, and subjected to emulsification in a high shearing emulsifier (6,500 rpm, 3 min) so as to obtain a s/o primary emulsion. The primary emulsion was added into 1,000 ml of a 0.5% PVA solution at 6° C., under homogenization at 1,800 rpm, and then it was homogeneously emulsified for 2 min to obtain an S/O/W double emulsion. The double emulsion was stirred to volatilize and remove the organic solvent; the residue was washed and freeze-dried to obtain powdery microspheres. The microspheres had a drug loading amount of 2.12% and an entrapment efficiency of 52.4%.

Test Example 1: Entrapment Efficiency Tests of Examples and Comparative Examples Test method: 25 mg of goserelin reference was weighed and dissolved in distilled water to form a goserelin solution at a concentration of 0.02 mg/ml to be used as reference solution. In a 10 ml of volumetric flask, 20 mg of goserelin microspheres was dissolved in appropriate amount of pure acetic acid and diluted with distilled water to reach the volume to make a test solution. Then the sample was subjected to high speed centrifugation, and the supernatant was directly injected into high performance liquid chromatography (HPLC).

The chromatographic column: $C_{18}$ column (25 cm×4.6 mm, 5 μm);

column temperature: 40° C.±0.5° C.

Mobile phase: 0.5% of phosphoric acid acetonitrile solution—0.5% of phosphoric acid solution (25:75) (V:V)

Flow rate: 1.0 ml/min;
Detection wavelength: 220 nm;
Sampling volume: 10 μl

10 μl of the test solution and 10 μl of the reference solution were injected into the liquid chromatograph. Then the chromatographic peak retention time and chromatographic peak areas were measured and recorded to calculate the amount of goserelin in microspheres by external standard method, and the entrapment efficiency can be calculated through the aforesaid formula. The entrapment efficiency of the test examples and the reference sample are shown in Table 1.

TABLE 1

Results of entrapment efficiency in test examples and Control groups

| Example No. | Entrapment Efficiency | Amount of Poloxamer or PEG |
|---|---|---|
| Example 1 | 90.1% | 10.00% |
| Example 2 | 90.7% | 7.95% |
| Example 3 | 90.1% | 1.05% |
| Example 4 | 91.4% | 1.04% |
| Example 5 | 98.6% | 2.05% |
| Example 6 | 91.3% | 5.04% |
| Example 7 | 90.2% | 9.97% |
| Example 8 | 97.3% | 1.98% |
| Example 9 | 95.8% | 3.08% |
| Example 10 | 98.0% | 3.96% |
| Example 11 | 76.1% | 0.30% |
| Example 12 | 92.9% | 1.99% |
| Example 13 | 90.1% | 2.04% |
| Example 14 | 90.4% | 2.04% |
| Comparative Example 1 | 52.4% | no |

Table 1 shows that the entrapment efficiency of the microspheres can reach to 90% and above if the goserelin microspheres were prepared from goserelin pretreated by Poloxamer/PEG and the content by weight of Poloxamer/PEG in the goserelin microspheres is above 1%. The entrapment efficiency of the microspheres containing no poloxamer/PEG is about 50%.

Test Example 2: In Vivo Release Test of Goserelin Microspheres Comprising Poloxamer/PEG with Different Contents and No Poloxamer/PEG Test Materials:

Test drugs: goserelin microspheres prepared according to Examples 11, 4, 5, 6 and 7, which contain 0.3% (w/w), 1% (w/w), 2% (w/w), 5% (w/w), 10% (w/w) of Poloxamer 188, respectively. goserelin microspheres prepared according to Example 12, which contain 2% PEG6000. PLGA used in the samples are PLGA (50/50, 0.14, 7,200).

Control group: goserelin microspheres containing no poloxamer/PEG and with a drug loading amount of about 2.42% prepared according to Comparative Example 1.

Experimental Animals:

SD rats (Shandong Luye Pharmaceutical Co., Ltd. Animal Room).

Test Instruments:

a QTRAP5500 mass spectrometer fitted with an ionspray ionization source (Applied Biosystem, Inc.);

an Agilent 1290 high performance liquid chromatography system comprising a dual infusion pump, an autosampler and a column oven;

an Anke TGL-16G Feige desk centrifuge, (ShangHai Anting Scientific Instrument Factory); and a Turbo Vap LV pressure blowing concentrator, (Biotage, Inc).

Test Method:

a) Experimental animals: male SD rats with body weight of 190±10 g, 4 per group;

b) Route of administration and dose: intramuscular injection at a dose of 0.9 mg/per rat and at a volume of 0.5 mL/per rat.

c) Blood sampling time: blood samples were collected before (at 0 h) and after administration at 1 h, 6 h, 1 d, 4 d, 7 d, 9 d, 11 d, 13 d, 15 d, 17 d, 19 d, 23 d and 28 d, respectively.

d) Determination of biological samples: the free drug concentration of goserelin in blood plasma was determined by an LC-MS/MS method;

e) Data processing: DAS 2.0 software.

Results are shown in Table 2 and FIG. 1.

TABLE 2

Blood concentrations of goserelin at different time after intramuscular injection to rats (ng/mL)

| Time (Day) | Comparative Example 1 | Example 11 | Example 4 | Example 5 | Example 6 | Example 7 | Example 12 |
|---|---|---|---|---|---|---|---|
| 0 | 0 | 0 | 0 | 0 | 0 | 0 | 0 |
| 0.04 | 150.25 | 31.23 | 30.60 | 51.12 | 43.32 | 42.57 | 43.02 |
| 0.25 | 6.17 | 1.24 | 2.10 | 2.12 | 2.71 | 1.43 | 1.58 |
| 1 | 1.58 | 1.15 | 1.81 | 1.13 | 2.54 | 0.95 | 2.86 |
| 4 | 4.42 | 4.02 | 3.62 | 5.82 | 6.24 | 4.98 | 5.72 |
| 7 | 4.74 | 3.50 | 6.45 | 9.27 | 10.87 | 10.29 | 10.52 |
| 9 | 5.60 | 7.57 | 8.86 | 10.96 | 8.96 | 10.44 | 10.48 |
| 11 | 1.37 | 4.72 | 5.25 | 6.78 | 5.48 | 5.89 | 6.02 |
| 13 | 0.24 | 3.76 | 2.91 | 3.12 | 2.39 | 3.46 | 1.95 |
| 15 | 0.02 | 2.51 | 2.12 | 2.63 | 1.80 | 2.10 | 1.32 |
| 17 | 0 | 1.51 | 1.51 | 1.65 | 1.12 | 1.13 | 0.73 |

TABLE 2-continued

Blood concentrations of goserelin at different time
after intramuscular injection to rats (ng/mL)

| Time (Day) | Comparative Example 1 | Example 11 | Example 4 | Example 5 | Example 6 | Example 7 | Example 12 |
|---|---|---|---|---|---|---|---|
| 19 | 0 | 0.38 | 0.38 | 0.31 | 0.73 | 0.13 | 0.20 |
| 23 | 0 | 0.24 | 0.24 | 0.20 | 0.22 | 0.28 | 0.19 |
| 28 | 0 | 0 | 0 | 0.02 | 0.01 | 0.02 | 0.01 |
| AUC (ng/ml * h) | 1542.1 | 1661.4 | 1875.2 | 2455.7 | 2401.9 | 2308.7 | 2338.5 |

The results show that the goserelin microspheres released drugs immediately after administration, and the AUC of the goserelin microspheres containing poloxamer/PEG was significantly higher than those containing no poloxamer/PEG. Thus, the presence of poloxamer/PEG in the goserelin microspheres was shown to increase the in vivo bioavailability. Further, the bioavailability of the microspheres was shown to be relevant to the content of poloxamer/PEG in the microspheres. When the content of Poloxamer/PEG in goserelin microspheres is above 1%, the bioavailability of the goserelin microspheres increases more than 20% compared with the goserelin microspheres containing no poloxamer/PEG.

Example 15

92 mg of goserelin acetate (containing 80 mg of goserelin as measured) and 6 mg of Poloxamer 188 were weighed and dissolved in 4 ml of water to form a clear solution, and then the solution was freeze-dried so as to obtain a mixture of solid powder. 1.902 g PLGA (50/50, 0.20, 16,000) was weighed and dissolved in 8 ml of dichloromethane to form an oil phase; and then the pretreated drug mixture of solid powder was added into the oil phase, and subjected to emulsification in a high shearing emulsifier (6,500 rpm, 3 min) so as to obtain a s/o primary emulsion. The primary emulsion was added into 1,000 ml of a 1.0% PVA solution at 6° C. under homogenization at 1,800 rpm, and then it was homogeneously emulsified for 2 min to obtain an S/O/W double emulsion. The double emulsion was stirred to volatilize and remove the organic solvent; the residue was washed and freeze-dried to obtain powdery microspheres. The microspheres had a drug loading amount of 2.76% and an entrapment efficiency of 74.6%.

Example 16

92 mg of goserelin acetate (containing 80 mg of goserelin as measured) and 20 mg of Poloxamer 188 were weighed and dissolved in 10 ml of water to form a clear solution, and then the solution was freeze-dried so as to obtain a mixture of solid powder. 1.888 g PLGA (50/50, 0.20, 16,000) was weighed and dissolved in 8 ml of dichloromethane to form an oil phase; and then the pretreated drug mixture of solid powder was added into the oil phase, and subjected to emulsification in a high shearing emulsifier (6,500 rpm, 3 min) so as to obtain a s/o primary emulsion. The primary emulsion was added into 1,000 ml of a 1.0% PVA solution at 6° C. under homogenization at 1,800 rpm, and then it was homogeneously emulsified for 2 min to obtain an S/O/W double emulsion. The double emulsion was stirred to volatilize and remove the organic solvent; the residue was washed and freeze-dried to obtain powdery microspheres. The microspheres had a drug loading amount of 3.49% and an entrapment efficiency of 90.1%.

Example 17

92 mg of goserelin acetate (containing 80 mg of goserelin as measured) and 39 mg of Poloxamer 188 were weighed and dissolved in 10 ml of water to form a clear solution, and then the solution was freeze-dried so as to obtain a mixture of solid powder. 1.870 g PLGA (50/50, 0.20, 16,000) was weighed and dissolved in 8 ml of dichloromethane to form an oil phase; and then the pretreated drug mixture of solid powder was added into the oil phase, and subjected to emulsification in a high shearing emulsifier (6,500 rpm, 3 min) so as to obtain a s/o primary emulsion. The primary emulsion was added into 1,000 ml of a 1.0% PVA solution at 6° C. under homogenization at 1,800 rpm, and then it was homogeneously emulsified for 2 min to obtain an S/O/W double emulsion. The double emulsion was stirred to volatilize and remove the organic solvent; the residue was washed and freeze-dried to obtain powdery microspheres. The microspheres had a drug loading amount of 3.67% and an entrapment efficiency of 95.7%.

Example 18

92 mg of goserelin acetate (containing 80 mg of goserelin as measured) and 70 mg of Poloxamer 188 were weighed and dissolved in 4 ml of water to form a clear solution, and then the solution was freeze-dried so as to obtain a mixture of solid powder. 1.838 g PLGA (50/50, 0.20, 16000) was weighed and dissolved in 8 ml of dichloromethane to form an oil phase; and then the pretreated drug mixture of solid powder was added into the oil phase, and subjected to emulsification in a high shearing emulsifier (6,500 rpm, 3 min) so as to obtain a s/o primary emulsion. The primary emulsion was added into 1000 ml of a 1.0% PVA solution at 6° C. under homogenization at, rpm, and then it was homogeneously emulsified for 2 min to obtain an S/O/W double emulsion. The double emulsion was stirred to volatilize and remove the organic solvent; the residue was washed and freeze-dried to obtain powdery microspheres. The microspheres had a drug loading amount of 3.74% and an entrapment efficiency of 99.3%.

Example 19

92 mg of goserelin acetate (containing 80 mg of goserelin as measured) and 121 mg of Poloxamer 188 were weighed and dissolved in 4 ml of water to form a clear solution, and then the solution was freeze-dried so as to obtain a mixture of solid powder. 1.786 g PLGA (50/50, 0.20, 16,000) was weighed and dissolved in 8 ml of dichloromethane to form an oil phase; and then the pretreated drug mixture of solid powder was added into the oil phase, and subjected to emulsification in a high shearing emulsifier (6,500 rpm, 3 min) so as to obtain a s/o primary emulsion. The primary emulsion was added into 1,000 ml of a 1.0% PVA solution at 6° C. under homogenization at 1,800 rpm, and then it was homogeneously emulsified for 2 min to obtain an S/O/W double emulsion. The double emulsion was stirred to volatilize and remove the organic solvent; the residue was washed and freeze-dried to obtain powdery microspheres. The microspheres had a drug loading amount of 3.38% and an entrapment efficiency of 91.2%.

Example 20

92 mg of goserelin acetate (containing 80 mg of goserelin as measured) and 201 mg of Poloxamer 188 were weighed and dissolved in 10 ml of water to form a clear solution, and then the solution was freeze-dried so as to obtain a mixture of solid powder. 1.693 g PLGA (50/50, 0.20, 16,000) was weighed and dissolved in 8 ml of dichloromethane to form an oil phase; and then the pretreated drug mixture of solid powder was added into the oil phase, and subjected to emulsification in a high shearing emulsifier (6,500 rpm, 3 min) so as to obtain a s/o primary emulsion. The primary emulsion was added into 1,000 ml of a 1.0% PVA solution at 6° C., under homogenization at 1,800 rpm, and then it was homogeneously emulsified for 2 min to obtain an S/O/W double emulsion. The double emulsion was stirred to volatilize and remove the organic solvent; the residue was washed and freeze-dried to obtain powdery microspheres. The microspheres had a drug loading amount of 3.51% and an entrapment efficiency of 90.1%.

Example 21

92 mg of goserelin acetate (containing 80 mg of goserelin as measured) and 70 mg of PEG6000 were weighed and dissolved in 4 ml of water to form a clear solution, and then the solution was freeze-dried so as to obtain a mixture of solid powder. 1.838 g PLGA (50/50, 0.20, 16,000) was weighed and dissolved in 8 ml of dichloromethane to form an oil phase; and then the pretreated drug mixture of solid powder was added into the oil phase, and subjected to emulsification in a high shearing emulsifier (6,500 rpm, 3 min) so as to obtain a s/o primary emulsion. The primary emulsion was added into 1,000 ml of a 1.0% PVA solution at 6° C. under homogenization at 1,800 rpm, and then it was homogeneously emulsified for 2 min to obtain an S/O/W double emulsion. The double emulsion was stirred to volatilize and remove the organic solvent; the residue was washed and freeze-dried to obtain powdery microspheres. The microspheres had a drug loading amount of 3.57% and an entrapment efficiency of 90.7%.

Comparative Example 2

92 mg of goserelin acetate (containing 80 mg of goserelin as measured) was weighed and dissolved in 4 ml of water to form a clear solution, and then the solution was freeze-dried so as to obtain a mixture of solid powder. 1.908 g PLGA (50/50, 0.20, 16,000) was weighed and dissolved in 8 ml of dichloromethane to form an oil phase; and then the pretreated drug mixture of solid powder was added into the oil phase, and subjected to emulsification in a high shearing emulsifier (6,500 rpm, 3 min) so as to obtain a s/o primary emulsion. The primary emulsion was added into 1,000 ml of a 1.0% PVA solution at 6° C. under homogenization at 1,800 rpm, and then it was homogeneously emulsified for 2 min to obtain an S/O/W double emulsion. The double emulsion was stirred to volatilize and remove the organic solvent; the residue was washed and freeze-dried to obtain powdery microspheres. The microspheres had a drug loading amount of 2.86% and an entrapment efficiency of 57.1%.

Test Example 3: In Vivo Release Test of Goserelin Microspheres Comprising Poloxamer/PEG with Different Contents and No Poloxamer/PEG Test Materials:

Test drugs: goserelin microspheres prepared according to Examples 15, 16, 17, 18, 19 and 20, which contain 0.3% (w/w), 1% (w/w), 2% (w/w), 3.5% (w/w), 6.0% (w/w) and 10% (w/w) of Poloxamer 188, respectively. Goserelin microspheres prepared according to Example 21, which contain 3.5% PEG6000. Polymers used in the samples are all PLGA (50/50, 0.20, 16,000).

Control group: goserelin microspheres containing no poloxamer/PEG and with a drug loading amount of about 2.74% prepared according to Comparative Example 2.

Experimental Animals:

SD rats (Shandong Luye Pharmaceutical Co., Ltd Animal Room).

Test Instruments:

a QTRAP5500 mass spectrometer fitted with an ionspray ionization source (Applied Biosystem, Inc.);

an Agilent 1290 high performance liquid chromatography system comprising a dual infusion pump, an autosampler and a column oven;

an Anke TGL-16G Feige desk centrifuge, (ShangHai Anting Scientific Instrument Factory); and a Turbo Vap LV pressure blowing concentrator, (Biotage, Inc).

Test Method:
a) Experimental animals: male SD rats with body weight of 190±10 g, 4 per group;
b) Route of administration and doses: intramuscular injection at a dose of 0.9 mg/per rat and at a volume of 0.5 mL/per rat.
c) Blood sampling time: blood samples were collected before (at 0 h) and after administration at 1 h, 6 h, 1 d, 4 d, 7 d, 9 d, 11 d, 13 d, 15 d, 17 d, 19 d, 23 d and 28 d, respectively.
d) Determination of biological samples: the free drug concentration of goserelin in the blood plasma was determined by an LC-MS/MS method;
e) Data processing: DAS 2.0 software.

Figure 2:
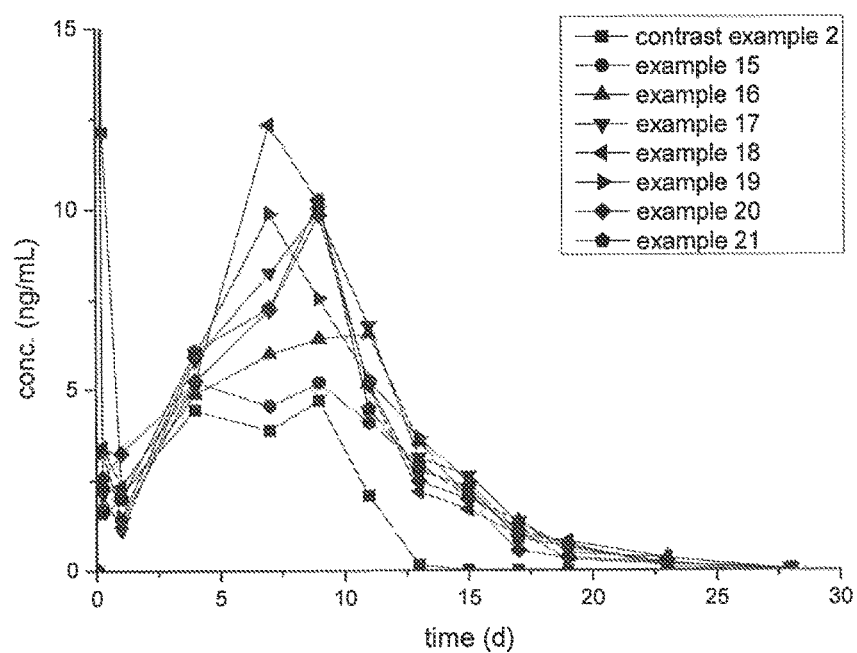
FIG. 2 is a graph of rat in vivo drug release curves of goserelin microspheres which contain different amount of poloxamer or PEG.

Results are shown in Table 3 and FIG. 2.

TABLE 3

Blood concentrations of goserelin at different time after intramuscular injection to rats (ng/mL)

| Time (Day) | Example 2 | Example 15 | Example 16 | Example 17 | Example 18 | Example 19 | Example 20 | Example 21 |
|---|---|---|---|---|---|---|---|---|
| 0 | 0 | 0 | 0 | 0 | 0 | 0 | 0 | 0 |
| 0.04 | 117.21 | 26.91 | 27.48 | 34.31 | 49.32 | 43.87 | 39.31 | 38.51 |
| 0.25 | 12.14 | 1.69 | 2.38 | 2.12 | 3.41 | 3.28 | 2.57 | 1.59 |
| 1 | 2.14 | 1.41 | 2.04 | 1.13 | 2.33 | 1.47 | 3.24 | 1.97 |
| 4 | 4.42 | 5.21 | 4.87 | 5.82 | 5.21 | 5.96 | 5.24 | 6.07 |
| 7 | 3.87 | 4.54 | 5.98 | 8.27 | 12.34 | 9.89 | 7.21 | 7.28 |
| 9 | 4.69 | 5.18 | 6.41 | 9.96 | 10.24 | 7.54 | 9.84 | 10.24 |
| 11 | 2.07 | 4.08 | 6.54 | 6.78 | 5.07 | 5.28 | 5.17 | 4.46 |
| 13 | 0.16 | 2.94 | 3.54 | 3.12 | 2.17 | 3.67 | 2.47 | 2.77 |
| 15 | 0.01 | 2.04 | 2.01 | 2.63 | 1.69 | 2.46 | 1.97 | 2.31 |
| 17 | 0 | 1.11 | 1.37 | 1.35 | 0.97 | 1.08 | 0.54 | 0.89 |
| 19 | 0 | 0.74 | 0.49 | 0.62 | 0.81 | 0.31 | 0.36 | 0.67 |
| 23 | 0 | 0.08 | 0.34 | 0.19 | 0.34 | 0.17 | 0.21 | 0.21 |
| 28 | 0 | 0 | 0 | 0.05 | 0.02 | 0.01 | 0.01 | 0.01 |
| AUC (ng/ml * h) | 1470.38 | 1605.06 | 1916.41 | 2305.88 | 2470.51 | 2260.72 | 2111.89 | 2159.99 |

The results show that the goserelin microspheres released drugs immediately after administration, and the AUC of the goserelin microspheres containing poloxamer/PEG was significantly higher than those containing no poloxamer/PEG. Thus, the presence of poloxamer/PEG in goserelin microspheres was shown to increase the in vivo bioavailability. Further, the bioavailability of the microspheres was shown to be relevant to the content of poloxamer/PEG in the microspheres. When the content of Poloxamer/PEG in goserelin microspheres is above 1%, the bioavailability of the goserelin microspheres increases more than 20% compared with the goserelin microspheres containing no poloxamer/PEG.

Example 22

9.2 g of goserelin acetate (containing 8 g of goserelin as measured) and 7.0 g of Poloxamer 188 were weighed and dissolved in 400 ml of water to form a clear solution, and then the solution was freeze-dried so as to obtain a mixture of solid powder (measuring the content of acetic acid in the intermediate, i.e., the freeze-dried powder of goserelin acetate and poloxamer; the test method is shown in test Example 4). 183.8 g PLGA (50/50, 0.20, 16,000) was weighed and dissolved in 800 ml of dichloromethane to form an oil phase; and then the pretreated drug mixture of solid powder was added into the oil phase, and subjected to emulsification in a high shearing emulsifier (6,500 rpm, 3 min) so as to obtain a s/o primary emulsion. The primary emulsion was added into 100 L of a 1.0% PVA solution at 6° C. under homogenization at 1,800 rpm, and then it was homogeneously emulsified for 2 min to obtain an S/O/W double emulsion. The double emulsion was stirred to volatilize and remove the organic solvent; the residue was washed and freeze-dried to obtain powdery microspheres. The microspheres had a drug loading amount of 3.73% and an entrapment efficiency of 97.4%.

Example 23

9.2 g of goserelin acetate (containing 8 g of goserelin as measured) and 7.0 g of Poloxamer 188 were weighed and dissolved in 400 ml of water to form a clear solution, and then the solution was freeze-dried so as to obtain a mixture of solid powder (measuring the content of acetic acid in the intermediate, i.e., the freeze-dried powder of goserelin acetate and poloxamer; the test method is shown in test Example 4; extending the freeze-drying time and raising temperature until the detected content of acetic acid is no more than 0.5%). 183.8 g PLGA (50/50, 0.20, 16,000) was weighed and dissolved in 800 ml of dichloromethane to form an oil phase; and then the pretreated drug mixture of solid powder was added into the oil phase, and subjected to emulsification in a high shearing emulsifier (6,500 rpm, 3 min) so as to obtain a s/o primary emulsion. The primary emulsion was added into 100 L of a 1.0% PVA solution at 6° C. under homogenization at 1,800 rpm, and then it was homogeneously emulsified for 2 min to obtain an S/O/W double emulsion. The double emulsion was stirred to volatilize and remove the organic solvent; the residue was washed and freeze-dried to obtain powdery microspheres. The microspheres had a drug loading amount of 3.71% and an entrapment efficiency of 99.6%.

Example 24

9.2 g of goserelin acetate (containing 8 g of goserelin as measured) and 7.0 mg of Poloxamer 188 were weighed and dissolved in 400 ml of 0.1% of ammonia water to form a clear solution, and then the solution was freeze-dried so as to obtain a mixture of solid powder (measuring the content of acetic acid in the intermediate, i.e., the freeze-dried powder of goserelin acetate and poloxamer; the test method is shown in test Example 4). 183.8 g PLGA (50/50, 0.20, 16,000) was weighed and dissolved in 800 ml of dichloromethane to form an oil phase; and then the pretreated drug mixture of solid powder was added into the oil phase, and subjected to emulsification in a high shearing emulsifier (6,500 rpm, 3 min) so as to obtain a s/o primary emulsion. The primary emulsion was added into 100 L of a 1.0% PVA solution at 6° C. through an injector under homogenization at 1,800 rpm, and then it was homogeneously emulsified for 2 min to obtain an S/O/W double emulsion. The double emulsion was stirred to volatilize and remove the organic solvent; the residue was washed and freeze-dried to obtain powdery microspheres. The microspheres had a drug loading amount of 3.73% and an entrapment efficiency of 99.4%.

Test Example 4: Influence of Different Content of Acetic Acid in Goserelin Microspheres on the In Vivo Release Amount Test method: determine with gas chromatography [Appendix VE, Method 3, of Chinese Pharmacopoeia (second part, 2000 Edition)].

Chromatographic Conditions and System Suitability Test

The column was a 10 meters long capillary column with inner diameter of 0.32 mm, and the inner layer was coated with 0.33 μm of FFAP-CB fused silica. The chromatographic conditions were set as follows:
Injection temperature: 220° C.;
Detector temperature: 250° C.;
Split ratio: 100:1;
The column temperature program was set as follows:
(1) starting at temperature of 50° C., and remained the same for 0.10 minutes;
(2) increasing the temperature at a rate of 30° C./min;
(3) the final temperature of 230° C., and remained for 5 minutes;
Injection volume: 1 μl;

The number of theoretical plates: calculated according to acetate peak and should not be less than 5000. The resolution of acetic acid peak and the internal standard peak should conform to the specifications.

Determination of the Correction Factor 1.0 ml n-hexadecane was precisely weighted and dissolved in 30 ml of dimethylformamide in a 50 ml volumetric flask, diluted to volume and shaken well to be used as internal standard solution. 625 mg of acetic acid reference was precisely weighted and dissolved in dimethylformamide in a 100 ml volumetric flask, diluted to volume and shaken well before use. 10 ml of the aforesaid solution was transferred into a 100 ml volumetric flask. 5 ml of the internal standard solution was added. The solution was dissolved with dimethylformamide and diluted to volume and shaken well. 1 μl of the solution was injected into gas chromatography and injected continually for 3-5 times. The correction factor was calculated according to average peak area.

Test Sample Preparation and Measurement

About 50 mg of goserelin microspheres prepared according to Example 22, 23 and 24 was weighted and transferred into a 2 ml volumetric flask, into which 1 ml of dimethylformamide was added to dissolve the sample. 100 μl internal standard solution was added precisely and then the flask was brought to final volume with dimethylformamide and shaken well. 1 μl of the sample was injected into gas chromatograph. The result was calculated by internal standard method.

Results are shown in Table 4.

TABLE 4

| Test substance | Example 22 | Example 23 | Example 24 |
|---|---|---|---|
| The content of acetic acid in the solid powder | 2.79% | 0.47% | 0.36% |
| The content of acetic acid in the microspheres | 0.39% | 0.0057% | 0.0048% |

Figure 3:
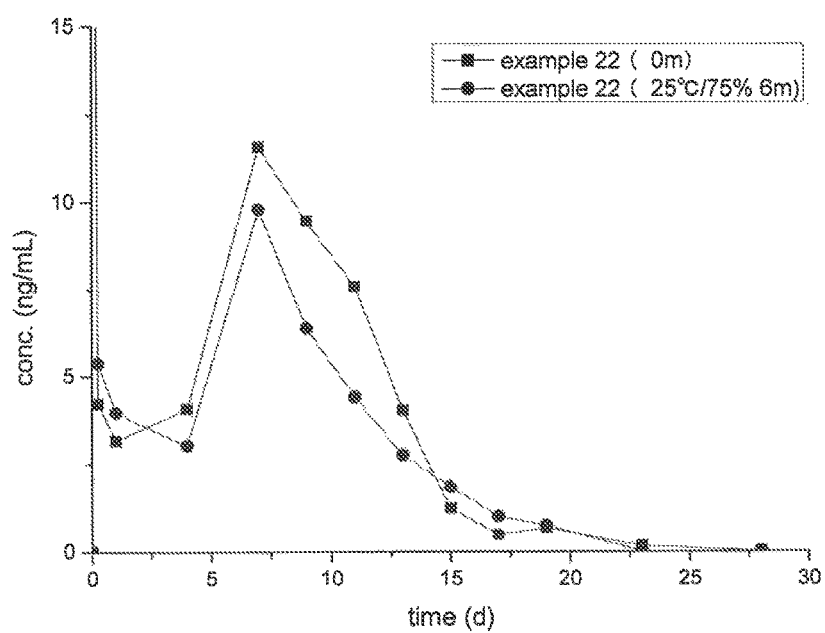
FIG. 3 is a graph of rat in vivo drug release curves of goserelin microspheres without control of the acetic acid content before and after the 6-month stability test.
Figure 4:
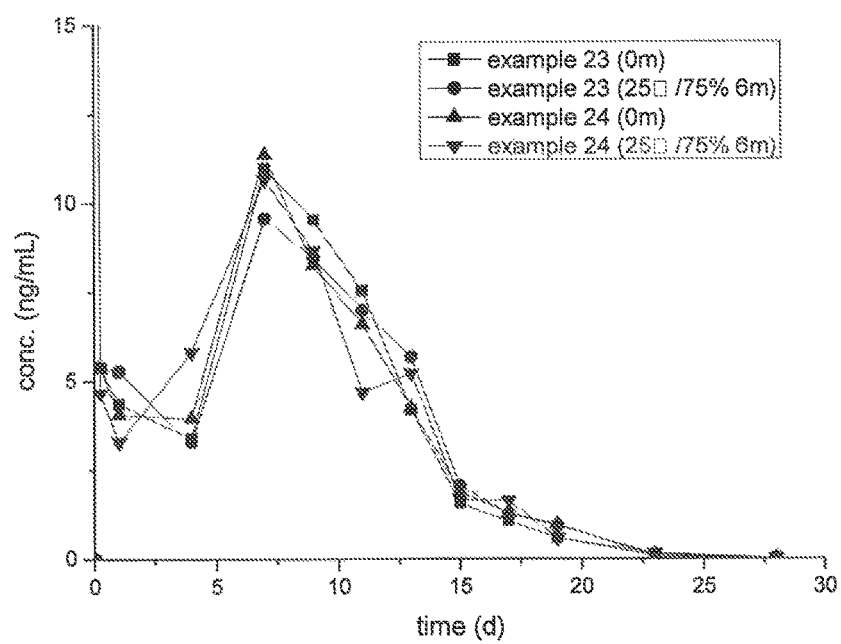
FIG. 4 is a graph of rat in vivo drug release profiles of goserelin microspheres with control of the acetic acid content before and after the 6-month stability test.

The goserelin microspheres in Example 22, 23 and 24 were studied for stability by conducting in vivo release test between samples immediately after prepared and samples stored for 6 months at temperature of 25° C. and humidity of 75%. The test method is showed in Test Example 2 and results are shown in Table 5 and FIGS. 3 and 4.

TABLE 5

Blood concentrations of goserelin at different time after intramuscular injection to rats (ng/mL)

| Time (Day) | Example 22 (0 month) | Example 22 (25° C./75%, 6 months) | Example 23 (0 month) | Example 23 (25° C./75%, 6 months) | Example 24 (0 month) | Example 24 (25° C./75%, 6 months) |
|---|---|---|---|---|---|---|
| 0 | 0 | 0 | 0 | 0 | 0 | 0 |
| 0.04 | 51.41 | 33.07 | 47.38 | 48.37 | 49.25 | 50.07 |
| 0.25 | 4.21 | 5.37 | 5.37 | 5.39 | 5.37 | 4.67 |
| 1 | 3.17 | 3.97 | 4.37 | 5.27 | 4.06 | 3.29 |
| 4 | 4.07 | 3.03 | 3.41 | 3.29 | 3.97 | 5.81 |
| 7 | 11.58 | 9.79 | 10.97 | 9.58 | 11.37 | 10.67 |
| 9 | 9.47 | 6.38 | 9.54 | 8.47 | 8.26 | 8.67 |
| 11 | 7.59 | 4.41 | 7.54 | 6.98 | 6.59 | 4.69 |
| 13 | 4.04 | 2.76 | 4.2 | 5.67 | 4.26 | 5.22 |
| 15 | 1.24 | 1.86 | 1.57 | 2.07 | 1.89 | 1.67 |
| 17 | 0.48 | 1.01 | 1.06 | 1.27 | 1.29 | 1.65 |
| 19 | 0.67 | 0.74 | 0.59 | 0.94 | 0.97 | 0.57 |
| 23 | 0.17 | 0.02 | 0.08 | 0.13 | 0.06 | 0.16 |
| 28 | 0.01 | 0.02 | 0.01 | 0.01 | 0.01 | 0.01 |
| AUC (ng/ml * h) | 2495.7 | 1989.98 | 2503.67 | 2512.33 | 2507.09 | 2520.61 |

The results show that control the content of acetic acid during the process of goserelin acetate microspheres of does not affect the drug loading amount and the entrapment efficiency. However, the in vivo drug release amount changed after the stability study (after stored for 6 months in condition of temperature of 25° C. and humidity of 75%). The in vivo drug release amount does not change when the content of acetic acid in goserelin microspheres is less than 0.01%, while the in vivo drug release amount of the goserelin microspheres decreases by more than 20% when the content of acetic acid in goserelin microspheres is not controlled Test Example 5 Measurement of the Particle Sizes of Solid Powder in Oil Phase and the Particle Sizes of Microspheres Prepared Test drugs: goserelin microspheres prepared according to Examples 15, 16, 17, 18, 19 and 20, which contain 0.3% (w/w), 1% (w/w), 2% (w/w), 3.5% (w/w), 6.0% (w/w) and 10% (w/w) of Poloxamer 188, respectively; goserelin microspheres prepared according to Example 21, which contain 2% (w/w) of PEG6000. PLGA used in the samples are 50/50, 0.20, 16,000.

Control group: goserelin microspheres containing no poloxamer/PEG and with a drug loading amount of about 2.74% prepared according to Comparative Example 2.

Test method: According to the related regulations on particle size and particle size distribution measurement method [The third method in Appendix XIX E of Chinese Pharmacopoeia (second part, 2010 Edition)], 0.1% Tween 20 solution was used as dispersing agent. About 120 ml Tween 20 solution was transferred into the sample dispersion device of a particle size analyzer, and the rotational speed controller was adjusted so that the stirring was at 2,100 rpm. The background of dispersing agent was measured first. Then 0.1 ml of primary emulsion and 50 mg of freeze-dried microspheres powder were added into the dispersing agent. After the samples were distributed evenly, the particle sizes were measured in parallel for three times and the average numbers were taken.

Results are shown in Table 6.

TABLE 6

| Example No. | Primary emulsion d (0.5) | Microspheres D(4, 3) | Microspheres (span) |
|---|---|---|---|
| Example 15 | 3.44 μm | 157.4 | 2.67 |
| Example 16 | 0.374 μm | 117.8 | 0.89 |
| Example 17 | 0.191 μm | 94.7 | 0.74 |
| Example 18 | 0.067 μm | 88.5 | 0.33 |
| Example 19 | 0.257 μm | 99.7 | 0.97 |
| Example 20 | 0.547 μm | 126.9 | 0.84 |
| Comparative Example 2 | 6.79 μm | 196.3 | 3.56 |

The results show that when preparing the microspheres, control of particle sizes of primary emulsion had significant effect on the particle sizes of the microspheres. When the particle sizes of the primary emulsion were controlled, the span of the goserelin microspheres could be ten times less than the situation when the particle sizes of the primary emulsion were not controlled. Therefore by controlling the particle sizes of the primary emulsion, more uniform sizes of microspheres product could be obtained.

What is claimed is:

1. A pharmaceutical composition of sustained release microspheres, comprising (a) goserelin or a salt thereof, (b) poly(lactide-co-glycolide), (c) poloxamer or polyethylene glycol (PEG), and (d) acetic acid, wherein the amount of acetic acid in the microspheres is less than 0.01% by weight.

2. The pharmaceutical composition according to claim 1, wherein the amount of poloxamer or PEG in the microspheres is within a range from 1% to 10% by weight.

3. The pharmaceutical composition according to claim 2, wherein the poloxamer is poloxamer 188 or poloxamer 407.

4. The pharmaceutical composition according to claim 2, wherein the PEG is PEG 2000, PEG 4000 or PEG 6000.

5. The pharmaceutical composition according to claim 1, wherein the amount of the poly(lactide-co-glycolide) in the microspheres is within a range from 80% to 98% by weight.

6. The pharmaceutical composition according to claim 1, wherein the molar ratio of lactide to glycolide in the poly (lactide-co-glycolide) is within a range from 90:10 to 10:90.

7. The pharmaceutical composition according to claim 6, wherein the molar ratio of lactide to glycolide in the poly (lactide-co-glycolide) is within a range from 60:40 to 40:60.

8. The pharmaceutical composition according to claim 7, wherein the molar ratio of lactide to glycolide in the poly (lactide-co-glycolide) is about 50:50.

9. The pharmaceutical composition according to claim 6, wherein the poly(lactide-co-glycolide) has an intrinsic viscosity of 0.10-0.40 dl/g.

10. The pharmaceutical composition according to claim 9, wherein the poly(lactide-co-glycolide) has an intrinsic viscosity of 0.15-0.30 dl/g.

11. The pharmaceutical composition according to claim 6, wherein the poly (lactide-co-glycolide) has a molecular weight of 4,000-45,000 Dalton.

12. The pharmaceutical composition according to claim 11, wherein the poly (lactide-co-glycolide) has a molecular weight of 10,000-25,000 Dalton.

13. The pharmaceutical composition according to claim 1, wherein the amount of the goserelin or a salt thereof in the microspheres is within a range from 1% to 10% by weight.

14. The pharmaceutical composition according to claim 1, wherein in the microspheres,
the amount of the goserelin is within a range from 1% to 10% by weight;
the amount of the poly(lactide-co-glycolide) is within a range from 80% to 98% by weight; and
the amount of the poloxamer or PEG is within a range from 1% to 10% by weight.

15. The pharmaceutical composition according to claim 14, wherein in the microspheres,
the amount of the goserelin is within a range from 1% to 8% by weight;
the amount of the poly(lactide-co-glycolide) is within a range from 86% to 98% by weight; and
the amount of the poloxamer or PEG is within a range from 1% to 6% by weight.

16. The pharmaceutical composition according to claim 15, wherein in the microspheres,
the amount of the goserelin is within a range from 1% to 5% by weight;
the amount of the poly(lactide-co-glycolide) is within a range from 91% to 98% by weight; and
the amount of the poloxamer or PEG is within a range from 1% to 4% by weight.

17. A method for preparing the pharmaceutical composition of claim 1, wherein the composition is prepared by a solid-in-oil-in-water (S/O/W) emulsion-solvent evaporation method, comprising pre-treating goserelin acetate with poloxamer or PEG, and then adding the pretreated goserelin acetate to an oil phase comprising poly(lactide-co-glycolide).

18. The method of claim 17, wherein the poloxamer or PEG pre-treated goserelin acetate in the oil phase has a particle size d (0.5) of 0.01-2 μm.

19. A method for treating prostate cancer, sexual precocity, adenomyosis, female infertility, or hysteromyoma in a subject in need thereof, comprising administering to the subject an effective amount of the pharmaceutical composition of claim 1.

* * * * *